(12) United States Patent
Wang

(10) Patent No.: US 6,660,856 B2
(45) Date of Patent: Dec. 9, 2003

(54) SYNTHESIS OF PYRROLO[2,1-C][1,4] BENZODIAZEPINE ANALOGUES

(75) Inventor: Jeh-Jeng Wang, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 10/094,140

(22) Filed: Mar. 8, 2002

(65) Prior Publication Data

US 2003/0187253 A1 Oct. 2, 2003

(51) Int. Cl.[7] .............................................. C07D 487/00
(52) U.S. Cl. ....................................................... 540/496
(58) Field of Search ......................................... 540/496

(56) References Cited

PUBLICATIONS

Hu et al. (J. Org. Chem. 2001, 66, 2881–2883).*

* cited by examiner

Primary Examiner—Bruck Kifle

(74) Attorney, Agent, or Firm—Ohlandt, Greeley, Ruggiero & Perle, L.L.P.

(57) ABSTRACT

The present invention provides an efficient process for the preparation of pyrrolo [2,1-c][1,4]benzodiazepines (PBDs) represented by the formula (I):

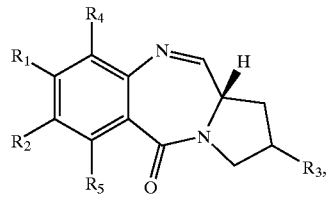

which starts from a subsituted 2-amino benzoic acid compound, and involves a step of an intermediate MOM-protected dilactam compound in the presence of $LiBH_4$. The process enables a practital and large scale (e.g. ca. 10 g) synthesis of PBD analogue.

35 Claims, No Drawings

SYNTHESIS OF PYRROLO[2,1-C][1,4] BENZODIAZEPINE ANALOGUES

BACKGROUND OF THE INVENTION

1) Field of the Invention

This invention relates to a novel process for synthesis of pyrrolo[2,1-c][1,4]benzodiazepine (PBD) analogues in a high yield. Specifically, this invention relates to a process for preparing PBD analogues starting from a substituted 2-amino benzoic acid, which enables a practical and large scale (e.g., ca. 10 g) synthesis of PBD analogues.

2) Description of the Related Art

Pyrrolo[2,1-c][1,4]benzodiazepines (PBDs) are a group of potent, naturally occurring anti-tumor antibiotics produced by Streptomyces species (M. D. Tendler et. al., *Nature* (1963), 199, 501; L. H. Hurley, *J. Antibiot.* (1977), 30, 349). The cytotoxic and antitumor effects of PBD compounds are believed to arise from their interaction with DNA molecules, which leads to inhibition of nucleic acid synthesis and production of excision-dependent single- and double-strand breaks in cellular DNA (K. W. Kohn, Anthramycin. In *Antibiotics III Mechanism of Action of Antimicrobial and Antitumor Agents*; ed. by J. W. Corcoran et. al. (Springer-Verlag, New York), pp. 3–11. (1975); R. L. Petrusek, et. al. *J. Biol. Chem.* 1982, 257, 6207). These antibiotics have been proposed to covalently bond to N2 of guanine to form a neutral minor groove adduct (L. H. Hurley et al., *Nature* (1979), 282, 529; S Cheatham et al., *Med. Chem.* (1988), 31, 583; J. J. Wang et al., *Med. Chem.* (1992), 35, 2995; J. A. Mountzouris et al., *J. Med. Chem.* (1994), 37, 3132).

Tomaymycin, cross-linker DSB-120 (J. A. Mountzouris et al., *J. Med. Chem.* (1994), 37, 3132; D. E. Thurston et al., *J. Org. Chem.* (1996), 61, 8141) and DC-81 (W. P. Hu et. al. *J. Org. Chem.* 2001, 66, 2881), the structure of which are shown below, are the best known examples of PBD analogues.

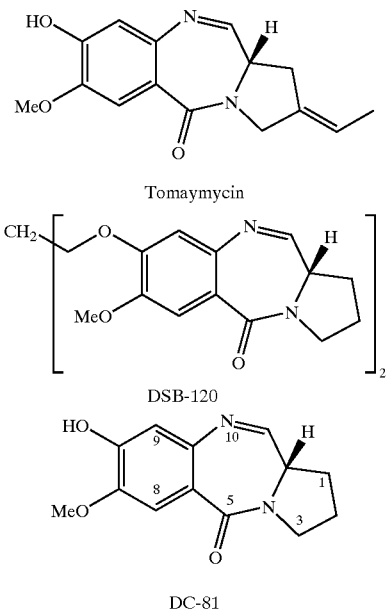

Tomaymycin

DSB-120

DC-81

Synthetic approaches of these PBD analogues have been reported (D. E. Thurston et. al. *Chem. Rev.* (1994), 94, 433 and references cited therein; A. Kamal et. al. *Tetrahedron Lett.* (2000), 41, 8631; T. Wang et. al. *Org. Lett.* (1999), 1, 1835.); however, most of them are tedious. For instance, the following scheme shows a widely used method which involves the cyclization of an amino dithioacetal (9) using mercuric chloride to yield an imine product.

Synthesis of DC-81 via Cyclization of Amino Dithioacetal

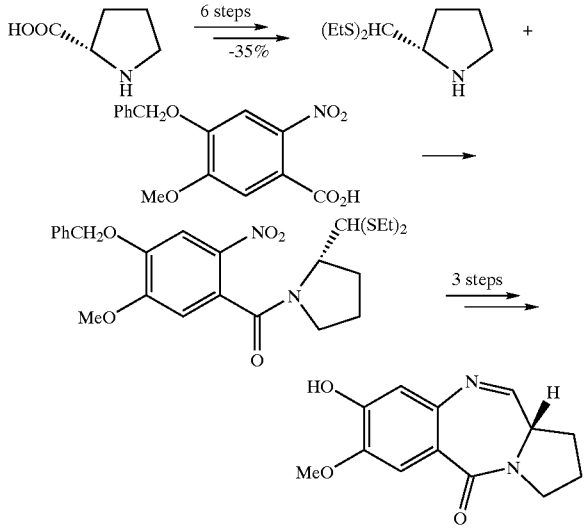

It is noted that it takes six steps to synthesize the starting material, i.e. (2S)-pyrrolidine-2-carboxaldehyde diethyl thioacetal, from L-proline. The overall yield of this 10-step synthesis process of DC-81 is about 15–20% (Thurston, D. E., et al., *J. Org. Chem.* (1996), 61, 8141. Thurston, D. E., et al., *Synthesis* (1990), 81). More recently, Wang et al. reported the total synthesis of DC-81 over 13 steps in 4% yield (Wang, T. et al., *Org. Lett.* (1999), 1, 1835).

Accordingly, there still exists a need to develop an efficient and practical process for the production of PBD analogues in a high yield.

SUMMARY OF THE INVENTION

Accordingly, in the first aspect, the present invention provides a process for preparing a compound of formula (I):

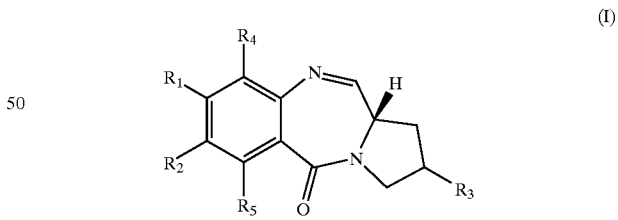

(I)

wherein $R_1$ and $R_2$ independently represent: hydrogen; halogen; amino; cyano; hydroxy; nitro; phenoxy; $C_1$–$C_{12}$ alkyl or $C_1$–$C_{12}$ alkoxy or $C_2$–$C_{12}$ alkenoxy optionally and independently substituted with halogen, amino, cyano, hydroxy, phenyl or $C_1$–$C_3$ alkoxy;

$R_3$ represents: hydrogen, or alkyl or alkenyl or alkenylidene, or R form or S form of hydroxyl or alkoxy; and $R_4$ and $R_5$ independently represent: hydrogen, halogen, cyano, hydroxy, phenoxy, $C_1$–$C_6$ alkyl or $C_1$–$C_6$ alkoxy optionally and independently substituted with halogen, amino, nitro, cyano, hydroxy, phenyl or $C_1$–$C_3$ alkoxy;

the process comprising the steps of:
(a) reacting a substituted 2-amino benzoic acid compound of formula (II) with triphosgen to form an isatoic anhydride compound of formula (III):

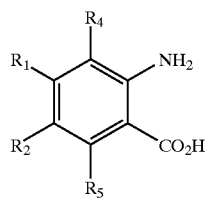
(II)

wherein
$R_1$ and $R_2$ independently represent: hydrogen; halogen; amino; cyano; nitro; phenoxy; $C_1$–$C_{12}$ alkyl or $C_1$–$C_{12}$ alkoxy or $C_2$–$C_{12}$ alkenoxy optionally and independently substituted with halogen, amino, cyano, hydroxy, phenyl or $C_1$–$C_3$ alkoxy; and $R_4$ and $R_5$ independently represent: hydrogen, halogen, cyano, hydroxy, phenoxy, $C_1$–$C_6$ alkyl or $C_1$–$C_6$ alkoxy optionally and independently substituted with halogen, amino, nitro, cyano, hydroxy, phenyl or $C_1$–$C_3$ alkoxy;

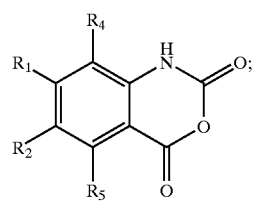
(III)

(b) coupling the isatoic anhydride compound of formula (III) from step (a) with an L-proline compound of formula (IV) to form a compound of formula (V):

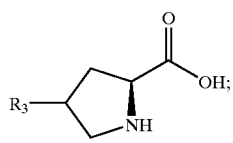
(IV)

wherein $R_3$ is hydrogen, hydroxyl, alkyl, alkenyl or alkenylidene or alkoxy;

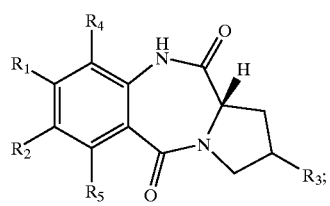
(V)

(c) converting the compound of formula (V) from step (b) to a compound of formula (VI) by reacting the compound of formula (V) with NaH, followed by reaction with methoxymethyl chloride (MOMCl):

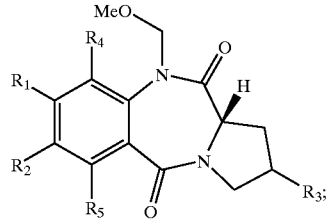
(VI)

and
(d) converting the compound of formula (VI) from step (c) to the compound of formula (I) by a reduction reaction in the presence of lithium borohydride ($LiBH_4$); and (e) when any one of $R_1$, $R_2$, $R_4$ and $R_5$ of the compound of formula (I) from step (d) is phenoxy or $C_1$–$C_{12}$ alkoxy substituted with phenyl, an optional step of converting said any one of $R_1$, $R_2$, $R_4$ and $R_5$ of formula (I) to a hydroxy group.

In a preferred embodiment, prior to step (a), the present process further includes an additional step of subjecting a substituted 2-nitrobenzoic acid of formula (IIA) to a reduction reaction to form the amine compound of formula (II):

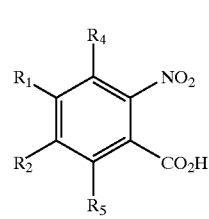
(IIA)

wherein $R_1$, $R_2$, $R_4$ and $R_5$ are the same as those defined for formula (II).

The reduction reaction of the additional step may be carried out: (1) by hydrogenation in the presence of a palladium-on-carbon system, (2) in the presence of an In/$NH_4Cl$ aqueous ethanol system, or (3) in the presence of a metal reducing agent selected from ferric chloride ($FeCl_3$) and stannous chloride ($SnCl_2$). In a more preferred embodiment, the reduction reaction of the additional step prior to step (a) of the present process is carried out in the presence of $SnCl_2$.

In a further preferred embodiment, the optional step (e) of the present process is carried out in the presence of 1,4-cyclohexadiene.

In a preferred embodiment, the present process produces a compound of formula (I) wherein both $R_4$ and $R_5$ are hydrogen.

In a further preferred embodiment, the present process produces a compound of formula (I), wherein $R_1$ and $R_2$ independently represent halogen, cyano, phenoxy, hydroxy, or $C_1$–$C_{12}$ alkyl or $C_1$–$C_{12}$ alkoxy optionally and independently substituted with halogen, amino, cyano, hydroxy, $C_1$–$C_3$ alkoxy or phenyl. Preferably, $R_1$ and $R_2$ independently represent hydroxy, or $C_1$–$C_{12}$ alkyl or $C_1$–$C_{12}$ alkoxy optionally and independently substituted with halogen, amino, cyano, hydroxy, $C_1$–$C_3$ alkoxy or phenyl.

In a more preferred embodiment, the present process produces a compound of formula (I), wherein one of $R_1$, $R_2$, $R_4$ and $R_5$ is halo(en, cyano, phenoxy, hydroxy or $C_1$–$C_{12}$ alkyl or $C_1$–$C_{12}$ alkoxy or $C_2$–$C_{12}$ alkenoxy optionally substituted with halogen, amino, cyano, hydroxy, $C_1$–$C_3$ alkoxy or phenyl, and the others are hydrogen.

In a more preferred embodiment, the present process produces a compound of formula (I), wherein both $R_4$ and $R_5$ s are hydrogen, and $R_1$ and $R_2$ independently represent halogen, cyano, phenoxy, hydroxy, or $C_1$-$C_{12}$ alkyl or $C_1$-$C_{12}$ alkoxy or $C_2$-$C_{12}$ alkenoxy optionally and independently substituted with halogen, amino, cyano, hydroxy, $C_1$-$C_3$ alkoxy or phenyl. Preferably, $R_1$ is benzyloxy and $R_2$ is methoxy. In a further preferred embodiment, $R_1$ is hydroxy and $R_2$ is methoxy.

In a preferred embodiment, the present process produces a compound of formula (I), wherein $R_3$ is hydrogen, ethylidene, or $R_3$ is R form or S form of hydroxyl or alkoxy.

In a more preferred embodiment, the present invention provides a process for preparing 8-hydroxy-7-methoxy-pyrrolo[2,1-c][1,4] benzodiazepin-5-one, comprising the steps of:

(a) subjecting 4-benzyloxy-5-methoxy 2-nitrobenzoic acid to a reduction reaction to form 2-amino-4-benzyloxy-5-methoxybenzoic acid;

(b) reacting the 2-amino-4-benzyloxy-5-methoxybenzoic acid from step (a) with triphosgen to form 7-benzyloxy-6-methoxy-isatoic anhydride;

(c) coupling the 7-benzyloxy-6-methoxy-isatoic anhydride from step (b) with L-proline to form 8-benzyloxy-7-methoxypyrrolo[2,1-c][1,4]benzodiazepine-5,11-dione;

(d) forming N-(10-methoxymethyl)-8-benzyloxy-7-methoxypyrrolo [2,1-c][1,4]benzodiazepine-5,11-dione by reacting the 8-benzyloxy-7-methoxypyrrolo [2,1-c][1,4]benzo-diazepine-5,11-dione from step (c) with NaH, followed by reaction with methoxymethyl chloride (MOMCl);

(e) converting the N-(10-methoxymethyl)-8-benzyloxy-7-methoxypyrrolo-[2,1-c][1,4]benzodiazepine-5,11-dione from step (d) to 8-benzyloxy-7-methoxy-pyrrolo [2,1-c][1,4]benzodiazepin-5-one via a reduction reaction in the presence of $LiBH_4$; and (f) reacting the 8-benzyloxy-7-methoxy-pyrrolo[2,1-c][1,4]benzo-diazepine 5-one from step (e) with 1,4-cyclohexadiene.

The above step (a) may be carried out in the presence of an In/$NH_4Cl$ aqueous ethanol system, or in the presence of a metal reducing agent selected from ferric chloride ($FeCl_3$) and stannous chloride ($SnCl_2$). In a preferred embodiment, the step (a) of the present process is carried out in the presence of $SnCl_2$.

In a second aspect, the present invention provides a process for producing a compound of formula (I):

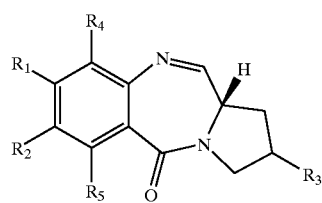

(I)

wherein $R_1$ and $R_2$ independently represent: hydrogen; halogen; amino; cyano; hydroxy; nitro; phenoxy; $C_1$-$C_{12}$ alkyl or $C_1$-$C_{12}$ alkoxy or $C_2$-$C_{12}$ alkenoxy optionally and independently substituted with halogen, amino, cyano, hydroxy, phenyl or $C_1$-$C_3$ alkoxy;

$R_3$ represents: hydrogen, or alkyl or alkenyl or alkenylidene, or R form or S form of hydroxyl or alkoxy; and $R_4$ and $R_5$ independently represent: hydrogen, halogen, cyano, hydroxy, phenoxy, $C_1$-$C_6$ alkyl or $C_1$-$C_6$ alkoxy optionally and independently substituted with halogen, amino, nitro, cyano, hydroxy, phenyl or $C_1$-$C_3$ alkoxy;

the process comprising the step of subjecting the compound of formula (VI) to a reduction reaction in the presence of lithium borohydride ($LiBH_4$):

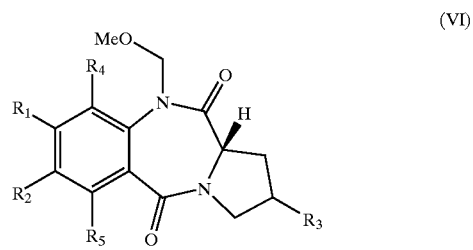

(VI)

wherein $R_1$ and $R_2$ independently represent: hydrogen; halogen; amino; cyano; nitro; phenoxy; $C_1$-$C_{12}$ alkyl or $C_1$-$C_{12}$ alkoxy or $C_2$-$C_{12}$ alkenoxy optionally and independently substituted with halogen, amino, cyano, hydroxy, phenyl or $C_1$-$C_3$ alkoxy; and $R_3$ is the same as that defined for formula (I);

$R_4$ and $R_5$ independently represent: hydrogen, halogen, cyano, hydroxy, phenoxy, $C_1$-$C_6$ alkyl or $C_1$-$C_6$ alkoxy optionally and independently substituted with halogen, amino, nitro, cyano, hydroxy, phenyl or $C_1$-$C_3$ alkoxy; and when any one of $R_1$, $R_2$, $R_4$ and $R_5$ of the resulting compound of (I) is phenoxy or $C_1$-$C_{12}$ alkoxy substituted with phenyl, an optional step of converting said any one of $R_1$, $R_2$, $R_4$ and $R_5$ of formula (I) to a hydroxy group.

DETAILED DESCRIPTION OF THIS INVENTION

This invention provides a very short route for efficient synthesis of PBD analogues, e.g. DC-81. The synthesis starts with the reaction of a substituted 2-amino benzoic acid with triphosgene in THF under reflux to form an isatoic anhydride compound, which is subsequently coupled with a substituted or unsubstituted L-proline compound in DMSO to produce a dilactam compound, followed by reaction with MOMCl. The resulting compound is then subjected to a reduction reaction in the presence of lithium borohydride ($LiBH_4$).

More specifically, according to this invention, there is provided a process for preparing a compound of formula (I):

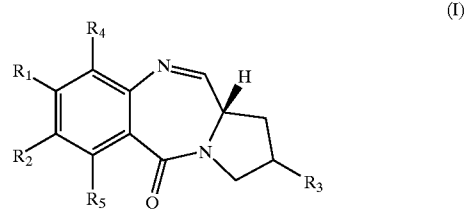

(I)

wherein $R_1$ and $R_2$ independently represent: hydrogen; halogen; amino; cyano; hydroxy; nitro; phenoxy; $C_1$–$C_{12}$ alkyl or $C_1$–$C_{12}$ alkoxy or $C_2$–$C_{12}$ alkenoxy optionally and independently substituted with halogen, amino, cyano, hydroxy, phenyl or $C_1$–$C_3$ alkoxy;

$R_3$ represents: hydrogen, or alkyl or alkenyl or alkenylidene, or R form or S form of hydroxyl or alkoxy; and $R_4$ and $R_5$ independently represent: hydrogen, halogen, cyano, hydroxy, phenoxy, $C_1$–$C_6$ alkyl or $C_1$–$C_6$ alkoxy optionally and independently substituted with halogen, amino, nitro, cyano, hydroxy, phenyl or $C_1$–$C_6$ alkoxy; the process comprising the steps of:

(a) reacting a substituted 2-amino benzoic acid compound of formula (II) with triphosgen to form an isatoic anhydride compound of formula (III):

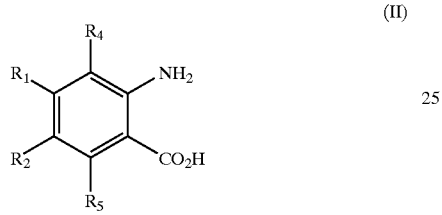

(II)

wherein $R_1$ and $R_2$ independently represent: hydrogen; halogen; amino; cyano; nitro; phenoxy; $C_1$–$C_{12}$ alkyl or $C_1$–$C_{12}$ alkoxy or $C_2$–$C_{12}$ alkenoxy optionally and independently substituted with halogen, amino, cyano, hydroxy, phenyl or $C_1$–$C_3$ alkoxy; and $R_4$ and $R_5$ independently represent; hydrogen, halogen, cyano, hydroxy, phenoxy, $C_1$–$C_6$ alkyl or $C_1$–$C_6$ alkoxy optionally and independently substituted with halogen, amino, nitro, cyano, hydroxy, phenyl or $C_1$–$C_3$ alkoxy;

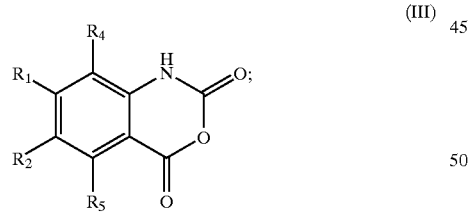

(III)

(b) coupling the isatoic anhydride compound of formula (III) from step (a) with an L-proline compound of formula (IV) to form a compound of formula (V):

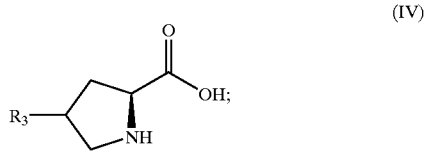

(IV)

wherein $R_3$ is hydrogen, hydroxyl, alkyl, alkenyl or alkenylidene or alkoxy;

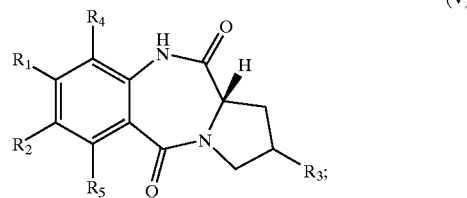

(V)

(c) converting the compound of formula (V) from step (b) to a compound of formula (VI) by reacting the compound of formula (V) with NaH, followed by reaction with methoxymethyl chloride (MOMCl):

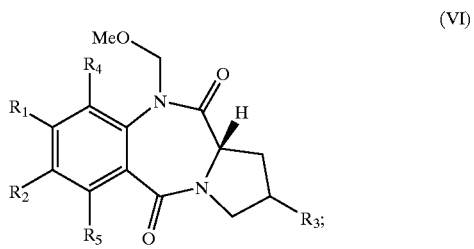

(VI)

and (d) converting the compound of formula (VI) from step (c) to the compound of formula (I) by a reduction reaction in the presence of lithium borohydride ($LiBH_4$); and (e) when any one of $R_1$, $R_2$, $R_4$ and $R_5$ of the compound of formula (I) from step (d) is phenoxy or $C_1$–$C_{12}$ alkoxy substituted with phenyl, an optional step of converting said any one of $R_1$, $R_2$, $R_4$ and $R_5$ of formula (I) to a hydroxy group.

The suitable compound of formula (II) for use in step (a) of the present process may be prepared according to known methods with reference to, e.g.,*J. Org. Chem.* USSR (1976), 12, 1045–1048; *J. Chem. Soc. Commu.* (1971) 567–572; *Chem. Ber.* (1913), 46, 3945; *Tetrahedron* (1967), 23, 4719; *Chem. Ber.* (1887), 20, 2441; *Tetrahedron Lett.* (1977), 3143; *Eur. J. Med. Chem. Chim. Ther.* (1999), 34 (9), 729–744 , *Justus Liebigs Ann Chem.* (1887), 237, 26; *Am. Chem. J.* (1889), 11, 7; and among others.

The suitable L-proline compound of formula (IV) for use in step (c) of the present process may be commercially available from, e.g. ACROS, or may be prepared according to known methods with reference to, e.g., *J. Chem. Soc.* (1965), 3850–3853; *J. Chem. Soc.* (1964), 5024–5029; *Chem. Pharm. Bull.* (1960) 8, 1110–1113; *Chem. Ber.* (1923) 56, 2214; *Collet. Czech. Chem. Commu.* (1995), 20 (1), 7; *Acta Phys. Chem.* (1957), 3, 118; Bull Chem. Soc. Jpn. (1981), 12, 3871–3872; *J. Biol. Chem.* (1952), 195, 383–384;*J. Biol. Chem.* (1953), 204, 307–313; *Isr. J. Chem.* (1974), 12, 165–166; *Helv. Chim. Acta* (1978), 61, 701–703; *JMC* (1967), 10, 1161–1162; *Chem. Abstr.*, 66, 11176; *Acta Chem. Scand.* (1990) 44 (3), 243–251; *Biochem. J.* (1941), 35, 461–462; *J. Biol. Chem.* (1934), 595–599; *JOC* (1985) 50 (19), 3457–3462; *JMC* (1991) 34 (2), 717–725; *Chem. Pharm. Bull.* (1997) 45 (2), 255–259; *Tetrahedron Letters* (1991), 32 (26), 3049–3050; *Tetrahedron Letters* (1993), 34 (15), 2477–2480; *J. Chem. Soc. Perkin Trans.* (1995), 10, 1251–1258; JMC (1988), 31 (6), 1148–1160; *Tetrahedron Letters* (1986), 27 (2), 151–154; *JOC*, (1989), 54 (8), 1857–1866; *Tetrahedron* (1993), 49 (33), 7239–7250; JMC (1988), 31 (6), 1148–1160; JOC (1995), 60 (9), 2925–2930;

JOC (1998), 63 (13), 4218–4227; *J. Chem. Soc. Chem. Commu.* (1987), 3, 166–168; *Chemical Review* (1994), 94 (2), pp. 454–455; and among others.

As an alternative, the substituted 2-amino benzoic acid of formula (II) used as a starting material of the present process may be obtained from a reduction of its corresponding substituted 2-nitrobenzoic acid (D. E. Thurston et al., *Synthesis* (1990), 81). Thus, prior to step (a), the present process may include an additional step of subjecting a substituted 2-nitrobenzoic acid of formula (IIA) to a reduction reaction to form the amine compound of formula (II):

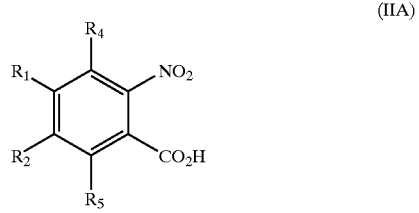

(IIA)

wherein $R_1$, $R_2$, $R_4$ and $R_5$ are the same as those defined for formula (II).

The reduction reaction of the additional step may be carried out: (1) by hydrogenation in the presence of a palladium-on-carbon system (K. C. Brown et al., *Syn Comm.* (1982), 12, 691), (2) in the presence of an In/NH$_4$Cl aqueous ethanol system (C. J. Moody et al., *Syn. Lett.* (1998), 1028), or (3) in the presence of a metal reducing agent selected from ferric chloride (FeCl$_3$) and stannous chloride (SnCl$_2$). In a preferred embodiment, the reduction reaction of the additional step prior to step (a) of the present process is carried out in the presence of SnCl$_2$.

When using a palladium-on-carbon system, the reduction reaction of the additional step may be conducted in a hydrogen atmosphere under a pressure of 2 ATM in the presence of 5% Pd/50% H$_2$SO4 (aq.)/glacial acetic acid.

The suitable compound of formula (IIA) for use in this additional step may be prepared according to known methods with reference to, e.g., D. E. Thurston et al., *Synthesis* (1990), 81; *J. Org. Chem.* USSR (Engl. transl.) (1976), 12, 1057–1060; *Tetrahedron*, (1967), 23, 4719–4727; *Acta Chem. Scand.* (1948), 34, 35; *Recl. Trav. Chim. Pays-Bas* (1929), 48, 139; *J. Med. Chem.* (1991) 34 (3), 1142–1154; *Chem. Pharm. Bull.* (1996), 44 (5), 1074; *Tetrahedron Letters* (1995). 36 (35), pp.6333–6336; *Tetrahedron* (1997), 53 (9), pp. 3223–3230; J. K. Still et al., *JACS* (1989), 111, 5417; *Bioorg. Med. Chem. Lett.* (1997), 7 (14), 1875–1878; *Eur. J. Med. Chem. Chim.* (1999), 34 (9), 729–744; and among others.

It is found that a key step of the present synthesis process may reside in the reduction of the MOM-protected compound of formula (VI). Mori et al., reported that the imine form of PBD analogues could be prepared via reduction of an MOM-protected dilactam with 10 molar equiv of NaBH$_4$ in MeOH at 0° C., followed by silica gel chromatography (M. Mori et al., *Tetrahedron Lett.* (1985), 26, 5947). Unfortunately, as reported by Thurston et al. (Langley, D. R.; Thurston, D. E *J. Org. Chem.* (1987), 52, 91), after the MOM-protected dilactam was prepared, it failed to afford the corresponding imine compound a structure of formula (I), using either the conditions reported by Mori et al. (supra), or a number of variations. Instead, ring-opening products were obtained via 3-aza-Grob fragmentation (J. J. Wang et al., *Tetrahedron* (1998), 54, 13149).

In light of straightforward reaction sequence consideration, the applicants of this invention explored this step with different reagents for conversion of compound of formula (VI) to its imine form. After careful study, it was found that the MOM-protected dilactam compound of formula (VI) was successfully converted to the compound of formula (I) by treating with LiBH$_4$ (1 molar equiv) in THF at -10° C. for 9 h. Further attempts to complete the reaction with longer reaction time, more reagents, or higher temperature would produce over-reduction amine products.

When any one of $R_1$, $R_2$, $R_4$ and $R_5$ of the compound of formula (I) is phenoxy or $C_1$–$C_{12}$ alkoxy substituted with phenyl, the present process may include a further step of converting said any one of $R_1$, $R_2$, $R_4$ and $R_5$ of formula (I) to a hydroxy group according to known methods. For example, in the following Example 6, benzyl DC-81 was converted to DC-81.

Another advantage of the present process is that the reactions can be carried out at much larger scale (10 g) than previously reported syntheses. Furthermore, in the first two steps, as well as the additional step prior to step (a), of the present process, the products were easily recrystallized and pure enough for subsequent reactions. The intermediate compound of formula (III) can serve as a versatile leaping point for further analogue synthesis to establish the SAR of substituted prolidine C ring.

The following Examples are given for the purpose of illustration only and are not intended to limit the scope of the present invention.

In the following Examples, melting points are uncorrected. $^1$H NMR and $^{13}$C NMR spectra were recorded at 400 and 100 MHz, respectively, using CDCl$_3$ as a solvent. $^1$H NMR chemical shifts are made with reference to TMS or CDCl$_3$ (7.26 ppm). $^{13}$C NMR was made with reference to CDCl$_3$ (77.0 ppm). Multiplicities were determined by the DEPT sequence as s, d, t, and q. Mass spectra and high-resolution mass spectra (HRMS) were measured using the electron-impact (EI, 70 eV) technique by Taichung Regional Instrument Center of the National Science Counsel (NSC) at National Chung-Hsing University (NCHU), Taiwan, ROC. Elemental analyses were performed by Tainan Regional Instrument Center of NSC at National Cheng-Kung University (NCKU), Taiwan, ROC. Flash chromatography was carried out on silica gel 60 (E. Merck, 230–400 mesh).

EXAMPLE 1

Synthesis of 2-Amino-4-benzyloxy-5-methoxybenzoic Acid

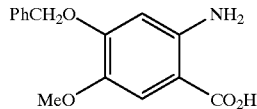

A solution of 4-benzyloxy-5-methoxy 2-nitrobenzoic acid (18.18 g, 60 mmol)(D. E. Thurston et al., *Synthesis* (1990), 81) and SnCl$_2$.2H$_2$O (137 g, 0.6 mol) (Showa Chemical Company, Japan) in MeOH (800 mL) was stirred at 70° C. for 5 h. The mixture was concentrated under vacuum to a thick syrup. Ethyl acetate (300 mL) was then added. The organic phase was washed with water until it turned to a clear solution, then washed with brine, and dried over MgSO$_4$. After removal of solvent, the crude was recrystallized from ethyl acetate to obtain the title compound in the form of a yellow solid with a yield of 15.1 g (92%).

Detected Properties of the Title Compound:

mp 159~161° C. $^1$H NMR (CDCl$_3$+DMSO-d$_6$, 400 MHz) δ 7.43~7.29 (m, 6H), 6.22 (s, 1H), 5.12 (s, 2H), 3.80 (s, 3H).

$^{13}$C NMR (CDC$_{13}$+DMSO-d$_6$, 100 MHz) δ 169.6 (s), 153.5 (s), 146.9 (s), 140.3 (s), 136.1 (s), 128.2 (d), 127.6 (d), 126.8 (d), 114.0 (d), 102.4 (s), 100.8 (d), 70.0 (t), 56.3 (q). LRMS (EI, m/z) 273 (M+). HRMS (EI, m/z) for C$_{15}$H$_{15}$NO$_4$, calcd. 273.1002, found 273.0995. Elem. Anal. for C$_{15}$H$_{15}$NO$_4$, calcd: C, 65.93; H, 5.53; N, 5.13; found: C, 65.67; H, 5.53; N, 4.89.

EXAMPLE 2

7-Benzyloxy-6-methoxy-isatoic Anhydride

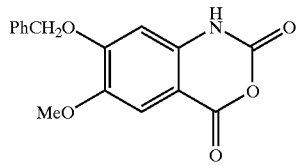

To a solution of the compound from Example 1 (20.1 g, 73.6 mmol) in THF (300 mL), triphosgene (16.2 g, 51.5 mmol) (purchased from Lancaster) was added in one portion. The reaction mixture was refluxed for 3 h. After cooled to room temperature, the solution was poured into ice/water. The resulting precipitate was filtered and recrystallized from MeOH to obtain the title compound in the form of a white solid with a yield of 21.5 g (98%).

Detected Properties of the Title Compound:

mp 232~235° C. $^1$H NMR (CDCl$_3$+DMSO-d$_6$, 400 MHz) δ 11.44 (s, NH), 7.47~7.33 (m, 6H), 6.74 (s, 1H), 5.21 (s, 2H), 3.89 (s, 3H). $^{13}$C NMR (CDCl$_3$+DMSO-d$_6$, 100 MHz) δ 159.5 (s), 156.0 (s), 147.9 (s), 146.4 (S), 137.6 (s), 135.3 (s), 128.6 (d), 128.3 (d), 127.6 (d), 109.2 (d), 101.7 (s), 99.4 (d), 70.9 (t), 56.2 (q). LRMS (EI, m/z) 299 (M+). HRMS (EI, m/z) for C$_{16}$H$_{13}$NO$_5$, calcd 299.0794, found 299.0792. Elem. Anal. for C$_{16}$H$_{13}$NO$_5$, calcd: C, 64.21; H, 4.38; N, 4.60; found: C, 63.99; H, 4.43; N, 4.50.

EXAMPLE 3

8-Benzyloxy-7-methoxypyrrolo[2,1-c][1,4] benzodiazepine-5,11-dione

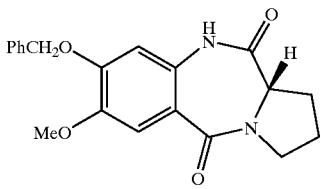

A mixture of the anhydride from Example 2 (15.9 g, 53.2 mmol) and L-proline (8.2 g, 68.4 mmol)(purchased from ACROS) in DMSO (300 mL) was heated at 120° C. for 4 h. After cooling to room temperature, the solution was poured into water (600 mL) and kept in a freezer (about −5° C.) for 6 h. The resulting precipitate was filtered and recrystallized from MeOH to obtain the title compound in the form of a white solid with a yield of 18.0 g (96%).

Properties of the Title Compound:

mp 190~193° C. $^1$H NMR (CDCl$_3$, 400 MHz) δ 8.07 (br s, NH), 7.43~7.33 (m, 5H), 7.27 (s, 1H), 6.45 (s, 1H), 5.17 (s, 2H), 4.30 (d, 3.2 Hz, 1H), 3.93 (s, 3H), 3.78~3.75 (m, 1H), 3.63~3.56 (m, 1H), 2.74~2.70 (m, 1H), 2.05~1.97 (m, 3H), $^{13}$C NMR (CDCl$_3$, 100 MHz) δ 170.8 (s), 165.2 (s), 151.4 (s), 147.0 (s), 135.9(s), 129.2 (s), 128.8 (d), 128.3 (d), 127.2 (d), 119.8 (s), 112.6 (d), 106.5(d), 71.1 (t), 56.8 (d),. 56.2 (q), 47.3 (t), 26.2 (t) 23.5 (t). LRMS (EI, m /z) 352 (M+). HRMS (EI, m/z) for C$_{20}$H$_{20}$N$_2$O$_4$, calcd 352.1424, found 352.1429. Anal. Calcd for C$_{20}$H$_{20}$N$_2$O$_4$: C, 68.17; H, 5.72; N, 7.95. Found; C, 68.01; H, 5.84; N, 7.80.

EXAMPLE 4

N-(10-Methoxymethyl)-8-benzyloxy-7-methoxypyrrolo[2,1-c][1,4]be nzodiazepine-5,11-dione

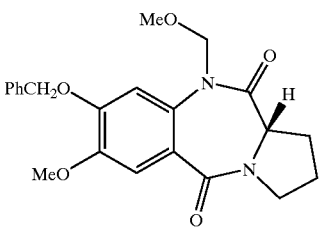

To a stirred solution of the compound from Example 3 (12 g, 34.1 mmol) in THF (150 mL), NaH (3.4 g, 85.3 mmol) (purchased from Lancaster) was added under nitrogen at 0° C., and the reaction mixture was stirred at the same temperature for 30 min. MOMCl (6.4 mL, 77.6 mmol) (purchased from TCI, Japan) was added dropwise into the reaction mixture. The resulting solution was stirred at room temperature for 24 h. The reaction mixture was poured into ice water (150 mL) and extracted four times with ethyl acetate. The combined organic phases were washed with saturated NaHCO$_3$, H$_2$O, brine, and dried over MgSO4. After removal of solvent, the residue was purified by flash chromatography (CH$_2$Cl$_2$/MeOH=40:1) to obtain the title compound in the form of a yellow oil with a yield of 12.2 g (90%).

Detected Properties of the Title Compound:

$^1$H NMR (CDCl$_3$, 400 MHz) δ 7.45~7.29 (m, 6H), 7.18 (s, 1H), 5.37 (d, J=10 Hz, 1H), 5.21 (s, 2H), 4.44 (d, J=10 Hz, 1 H), 4.09 (dd, J=8 and 2.4 Hz, 1H), 3.95 (s, 3H), 3.77~3.72 (m, 1H), 3.59~3.52 (m, 1H), 3.40 (s, 3H), 2.72~2.68 (m, 1H), 2.11~1.94 (m, 3H), $^{13}$C NMR (CDCl$_3$, 100 MHz) δ 170.3 (s), 165.1 (s), 150.7 (s), 147.5 (s), 136.0 (s), 133.7 (s), 128.6 (d), 128.1 (d), 127.4 (d), 122.3 (s), 111.5 (d), 107.1 (d), 79.7 (t), 71.0 (t), 57.5 (d), 56.8 (q), 56.2 (q), 46.7 (t), 26.5 (t) 23.7 (t). LRMS (EI, m/z) 396 (M+). HRMS (EI, m/z) for C$_{22}$H$_{24}$N$_2$O$_5$, calcd 396.1686, found 396.1688. Elem. Anal. for C$_{22}$H$_{24}$N$_2$O$_5$, calcd: C, 66.65; H, 6.10; N, 7.07; found: C, 66.42; H, 6.20; N, 6.85.

EXAMPLE 5

8-Benzyloxy-7-methoxy-pyrrolo[2,1-c][1,4] benzodiazepin-5-one (8-Benzyl DC-81)

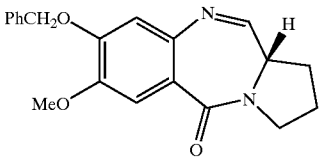

To a solution of the MOM-protected compound from Example 4 (9.6 g, 23.2 mmol) in THF (50 mL), lithium borohydride (516 mg, 23.2 mmol)(purchased from Merck) was added in one portion at −10° C., and the reaction mixture was stirred at the same temperature for 8 h. The reaction mixture was poured into ice water (100 mL) and extracted four times with ethyl acetate. The combined organic phases were washed with saturated $NaHCO_3$, $H_2O$, brine, and dried over $MgSO_4$. After removal of solvent, the residue was purified by flash chromatography ($CH_2Cl_2$/MeOH=70:1) to obtain the title compound in the form of a light yellow solid with a yield of 3.89 9 (50%), as swell as the MOM-protected compound of Example 4 (4.77 g)(95% yield based upon the recovered starting material).

Detected Properties of the Title Compound:

mp 58~61° C. $^1$H NMR ($CDCl_3$, 400 MHz) 67.47~7.29 (m, 6H), 7.18 (s, 1H), 5.38 (d, J=9.8 Hz, 1H), 5.21 (s, 2H), 4.45 (d, J=9.8 Hz, 1H), 4.12~4.07 (m, 1H), 3.95 (s, 3H), 3.75~3.54 (m, 2H), 3.40 (m, 3H), 2.70 (t, J=2.0 Hz, 1H), 2.06~1.95 (m, 4H), $^{13}$C NMR ($CDCl_3$, 100 MHz) δ 164.6 (s), 162.4 (d), 150.4 (s), 148.0 (s), 140.5 (s), 136.2 (s), 128.6 (d), 128.0 (d), 127.3 (d), 120.5 (s), 111.7 (d), 111.3 (d), 70.8 (t), 56.1 (q), 53.6(d), 46.6 (t), 29.6 (t) 24.1 (t). LRMS (EI, m/z) 336 (M+). HRMS (EI, m/z) for $C_{20}H_{20}N_2O_3$, calcd 336.1475, found 336.1473.

EXAMPLE 6

The compound of Example 5 may be further converted into 8-hydroxy-7-methoxypyrrolo[2,1-c][1,4]benzodiazepin-5-one (DC-81) in accordance with known methods, such as the one reported in D. E. Thurston et al., *Synthesis* (1990), 81. This example demonstrates the procedures of such conversion.

To a solution of the compound from Example 5 (5.93 g, 17.64 mmol) in absolute EtOH (130 mL), 10% Pd/C (8.8 9) was added under nitrogen. 1,4-Cyclohexadiene (17 mL, 176 mmol) was added to the solution dropwise. The resulting solution was stirred at room temperature for 2.5 h until TLC (reversed-phase $C_{18}$: $H_2O$/MeOH=1:3) indicated that the reaction was complete. The reaction mixture was filtered through Celite. Purification of the residue by flash chromatography ($CH_2Cl_2$/MeOH=40:1) resulted in a colorless solid product with a yield of 3.91 g (90%).

Detected Properties of the Product DC-81:

mp 135–138° C. $^1$H NMR ($CDCl_3$, 400 MHz) 67.67 (d, J) 4.4 Hz, 1H), 7.52 (s, 1H), 6.89 (s, 1H), 6.41 (br s, —OH), 3.96 (s, 3H), 3.85–8.79 (m, 1H), 3.74–3.70 (m, 1H), 3.61–3.54 (m, 1H), 2.35–2.29 (m, 2H), 2.09–2.01 (m, 2H); $^{13}$C NMR ($CDCl_3$, 100 MHz) (164.8 (s), 162.6 (d), 148.5 (s), 145.5 (s), 141.2 (s), 120.0 (s), 112.7 (d), 111.2 (d), 56.3 (q), 53.7 (d), 26.6 (t) 24.2 (t); LRMS (EI, m/z) 246 ($M_+$). HRMS (EI, m/z) for $C_{13}H_{14}N_2O_3$, calcd 246.1005, found 246.0996.

The above examples describe a practical and large-scale total synthesis of antibiotic DC-81. The efficiency and adaptability of the synthetic procedures detailed above make possible the application of this methodology to the preparation of other PBD analogues, such as Tomaymycin and DSB-120.

All literature references cited in the present specification are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

I claim:

1. A process for preparing a compound of formula (I):

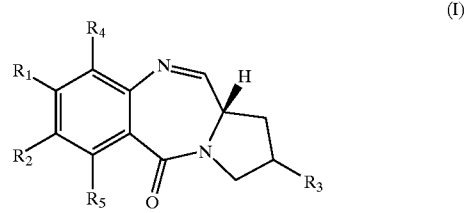

(I)

wherein $R_1$ and $R_2$ independently represent: hydrogen; halogen; amino; cyano; hydroxy; nitro; phenoxy; $C_1$–$C_{12}$ alkyl or $C_1$–$C_{12}$ alkoxy or $C_2$–$C_{12}$ alkenoxy optionally and independently substituted with halogen, amino, cyano, hydroxy, phenyl or $C_1$–$C_3$ alkoxy;

$R_3$ represents: hydrogen, or alkyl or alkenyl or alkenylidene, or R form or S form of hydroxyl or alkoxy; and $R_4$ and $R_5$ independently represent: hydrogen, halogen, cyano, hydroxy, phenoxy, $C_1$–$C_6$ alkyl or $C_1$–$C_6$ alkoxy optionally and independently substituted with halogen, amino, nitro, cyano, hydroxy, phenyl or $C_1$–$C_3$ alkoxy;

the process comprising the steps of:

(a) reacting a substituted 2-amino benzoic acid of formula (II) with triphosgen to form an isatoic anhydride compound of formula (III):

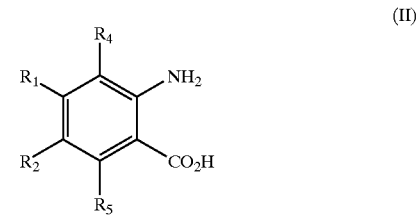

(II)

wherein $R_1$ and $R_2$ independently represent: hydrogen; halogen; amino; cyano; nitro; phenoxy; $C_1$–$C_{12}$ alkyl or $C_1$–$C_{12}$ alkoxy or $C_2$–$C_{12}$ alkenoxy optionally and independently substituted with halogen, amino, cyano, hydroxy, phenyl or $C_1$–$C_3$ alkoxy; and $R_4$ and $R_5$ independently represent: hydrogen, halogen, cyano, hydroxy, phenoxy, $C_1$–$C_6$ alkyl or $C_1$–$C_6$ alkoxy optionally and independently substituted with halogen, amino, nitro, cyano, hydroxy, phenyl or $C_1$–$C_3$ alkoxy;

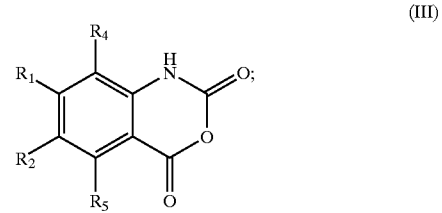

(III)

(b) coupling the isatoic anhydride compound of formula (III) from step (a) with an L-proline compound of formula (IV) to form a compound of formula (V):

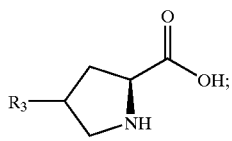

wherein R₃ is hydrogen, hydroxyl, alkyl, alkenyl or alkenylidene or alkoxy;

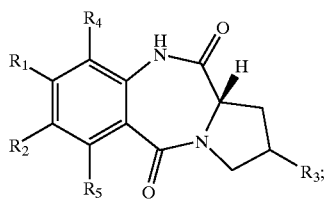

(c) converting the compound of formula (V) from step (b) to a compound of formula (VI) by reacting the compound of formula (V) with NaH, followed by reaction with methoxymethyl chloride (MOMCl):

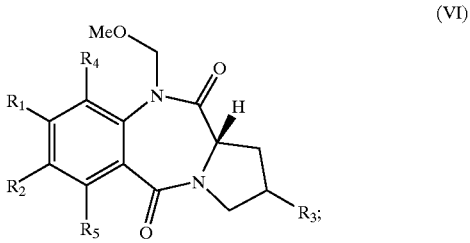

and (d) converting the compound of formula (VI) from step (c) to the compound of formula (I) by a reduction reaction in the presence of lithium borohydride (LiBH₄); and (e) when any one of $R_1$, $R_2$, $R_4$ and $R_5$ of formula (I) from step (d) is phenoxy or $C_1$–$C_{12}$ alkoxy substituted with phenyl, an optional step of converting said any one of $R_1$, $R_2$, $R_4$ and $R_5$ of formula (I) to a hydroxy group.

2. A process according to claim 1, wherein prior to step (a), the process further includes an additional step of subjecting a substituted 2-nitrobenzoic acid of formula (IIA) to a reduction reaction to form the amine compound of formula (II);

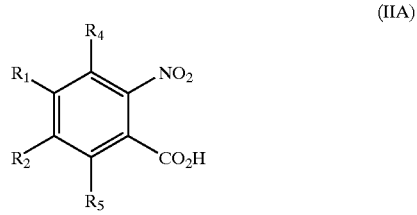

wherein $R_1$, $R_2$, $R_4$ and $R_5$ are the same as those defined for formula (II).

3. A process according to claim 2, wherein the reduction reaction of the additional step is carried out by hydrogenation in the presence of a palladium-on-carbon system.

4. A process according to claim 2, wherein the reduction reaction of the additional step is carried out in the presence of an In/NH₄Cl aqueous ethanol system.

5. A process according to claim 2, wherein the reduction reaction of the additional step is carried out in the presence of a metal reducing agent selected from ferric chloride (FeCl₃) and stannous chloride (SnCl₂).

6. A process according to claim 5, wherein the reduction reaction of the additional step is carried out in the presence of SnCl₂.

7. A process according to claim 1, wherein, in the compound of formula (I), both $R_4$ and $R_5$ are hydrogen or halogen.

8. A process according to claim 1, wherein, in the compound of formula (I), $R_1$ and $R_2$ independently represent halogen, cyano, phenoxy, hydroxy, or $C_1$–$C_{12}$ alkyl or $C_1$–$C_{12}$ alkoxy optionally and independently substituted with halogen, amino, cyano, hydroxy, $C_1$–$C_3$ alkoxy or phenyl.

9. A process according to claim 1, wherein, in the compound of formula (I), one of $R_1$, $R_2$, $R_4$ and $R_5$ is halogen, cyano, phenoxy, hydroxy or $C_1$–$C_{12}$ alkyl or $C_1$–$C_{12}$ alkoxy or $C_2$–$C_{12}$ alkenoxy optionally substituted with halogen, amino, cyano, hydroxy, $C_1$–$C_3$ alkoxy or phenyl, and the others are hydrogen.

10. A process according to claim 1, wherein, in the compound of formula (I), both $R_4$ and $R_5$ are hydrogen, and $R_1$ and $R_2$ independently represent halogen, cyano, phenoxy, hydroxy, or $C_1$–$C_{12}$ alkyl or $C_1$–$C_{12}$ alkoxy or $C_2$–$C_{12}$ alkenoxy optionally and independently substituted with halogen, amino, cyano, hydroxy, $C_1$–$C_3$ alkoxy or phenyl.

11. A process according to claim 10, wherein, in the compound of formula (I), $R_1$ is hydroxy and $R_2$ methoxy.

12. A process according to claim 10, wherein, in the compound of formula (I), $R_1$ is benzyloxy and $R_2$ methoxy.

13. A process according to claim 1, wherein, in the compound of formula (I), $R_1$ and $R_2$ independently represent hydroxy or methoxy.

14. A process according to claim 1, wherein, in the compound of formula (I), both $R_4$ and $R_5$ are hydrogen, and $R_1$ and $R_2$ independently represent hydroxy or methoxy.

15. A process according to claim 1, wherein, in the compound of formula (I), $R_3$ is hydrogen.

16. A process according to claim 1, wherein, in the compound of formula (I), $R_3$ is ethylidene.

17. A process according to claim 1, wherein, in the compound of formula (I), $R_1$ is R form or S form of hydroxyl or alkoxy.

18. A process according to claim 1, wherein the optional step (e) is carried out in the presence of 1,4-cyclohexadiene.

19. A process for preparing 8-hydroxy-7-methoxy-pyrrolo [2,1-c][1,4]benzodiazepin-5-one, comprising the steps of:
  (a) subjecting 4-benzyloxy-5-methoxy 2-nitrobenzoic acid to a reduction reaction to form 2-amino-4-benzyloxy-5-methoxybenzoic acid;
  (b) reacting the 2-amino-4-benzyloxy-5-methoxybenzoic acid from step (a) with triphosgen to form 7-benzyloxy-6-methoxy-isatoic anhydride,
  (c) coupling the 7-benzyloxy-6-methoxy-isatoic anhydride from step (b) with L-proline to form 8-benzyloxy-7-methoxypyrrolo [2,1-c][1,4]benzodiazepine-5,11-dione;
  (d) forming N-(10-methoxymethyl)-8-benzyloxy-7-methoxypyrrolo [2,1-c][1,4]benzodiazepine-5,1-dione by reacting the 8-benzyloxy-7-methoxypyrrolo[2,1-c][1,4]benzo-diazepine-5,11-dione from step (c) with NaH, followed by reaction with methoxymethyl chloride (MOMCl);

(e) converting the N-(10-methoxymethyl)-8-benzyloxy-7-methoxypyrrolo[2,1-c][1,4]benzodiazepine-5,11-dione from step (d) to 8-benzyloxy-7-methoxy-pyrrolo[2,1-c][1,4]benzodiazepin-5-one via a reduction reaction in the presence of LiBH$_4$; and (f) reacting the 8-Benzyloxy-7-methoxy-pyrrolo[2,1-c][1,4]benzodiazepin-5-one from step (e) with 1,4-cyclohexadiene.

20. A process according to claim 19, wherein the reduction reaction of step (a) is carried out in the presence of an In/NH$_4$Cl aqueous ethanol system.

21. A process according to claim 20, wherein the reduction reaction of step (a) is carried out using a reducing agent selected from ferric chloride (FeCl$_3$) and stannous chloride (SnCl$_2$).

22. A process according to claim 21, wherein the metal reducing agent employed in step (a) is SnCl$_2$.

23. A process for producing a compound of formula (I):

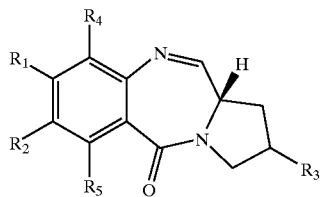

(I)

wherein $R_1$ and $R_2$ independently represent: hydrogen; halogen; amino; cyano; hydroxy; nitro; phenoxy; $C_1$–$C_{12}$ alkyl or $C_1$–$C_{12}$ alkoxy or $C_2$–$C_{12}$ alkenoxy optionally and independently substituted with halogen, amino, cyano, hydroxy, phenyl or $C_1$–$C_3$ alkoxy;

$R_3$ represents: hydrogen, or alkyl or alkenyl or alkenylidene, or R form or S form of hydroxyl or alkoxy; and $R_4$ and $R_5$ independently represent: hydrogen, halogen, cyano, hydroxy, phenoxy, $C_1$–$C_6$ alkyl or $C_1$–$C_6$ alkoxy optionally and independently substituted with halogen, amino, nitro, cyano, hydroxy, phenyl or $C_1$–$C_3$ alkoxy; the process comprising the step of subjecting the compound of formula (VI) to a reduction reaction in the presence of lithium borohydride (LiBH$_4$):

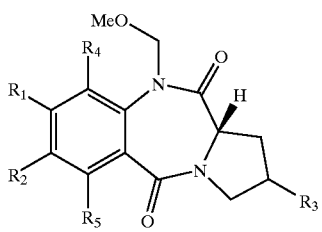

(VI)

wherein $R_1$ and $R_2$ independently represent, hydrogen; halogen; amino; cyano; nitro; phenoxy; $C_1$–$C_{12}$ alkyl or $C_1$–$C_{12}$ alkoxy or $C_2$–$C_{12}$ alkenoxy optionally and independently substituted with halogen, amino, cyano, hydroxy, phenyl or $C_1$–$C_3$ alkoxy; and $R_3$ is the same as defined that for formula (I);

$R_4$ and $R_5$ independently represent: hydrogen, halogen, cyano, hydroxy, phenoxy, $C_1$–$C_6$ alkyl or $C_1$–$C_6$ alkoxy optionally and independently substituted with halogen, amino, nitro, cyano, hydroxy, phenyl or $C_1$–$C_3$ alkoxy; and when any one of $R_1$, $R_2$, $R_4$ and $R_5$ of the resulting compound of formula (I) is phenoxy or $C_1$–$C_{12}$ alkoxy substituted with phenyl, an optional step of converting said any one of $R_1$, $R_2$, $R_4$ and $R_5$ of formula (I) to a hydroxy group.

24. A process according to claim 23, wherein, in the compound of formula (I), both $R_4$ and $R_5$ are hydrogen or halogen.

25. A process according to claim 23, wherein, in the compound of formula (I), $R_1$ and $R_2$ independently represent halogen, cyano, phenoxy, hydroxy, or $C_1$–$C_{12}$ alkyl or $C_1$–$C_{12}$ alkoxy optionally and independently substituted with halogen, amino, cyano, hydroxy, $C_1$–$C_3$ alkoxy or phenyl.

26. A process according to claim 23, wherein, in the compound of formula (I), one of $R_1$, $R_2$, $R_4$ and $R_5$ is halogen, cyano, phenoxy, hydroxy or $C_1$–$C_{12}$ alkyl or $C_1$–$C_{12}$ alkoxy or $C_2$–$C_{12}$ alkenoxy optionally substituted with halogen, amino, cyano, hydroxy, $C_1$–$C_3$ alkoxy or phenyl, and the others are hydrogen.

27. A process according to claim 23, wherein, in the compound of formula (I), both $R_4$ and $R_5$ are hydrogen, and $R_1$ and $R_2$ independently represent halogen, cyano, phenoxy, hydroxy, or $C_1$–$C_{12}$ alkyl or $C_1$–$C_{12}$ alkoxy or $C_2$–$C_{12}$ alkenoxy optionally and independently substituted with halogen, amino, cyano, hydroxy, $C_1$–$C_3$ alkoxy or phenyl.

28. A process according to claim 27, wherein, in the compound of formula (I), $R_1$ is hydroxy and $R_2$ is methoxy.

29. A process according to claim 27, wherein, in the compound of formula (I), $R_1$ is benzyloxy and $R_2$ is methoxy.

30. A process according to claim 23, wherein, in the compound of formula (I), $R_1$ and $R_2$ independently represent hydroxy or methoxy.

31. A process according to claim 23, wherein, in the compound of formula (I), both $R_4$ and $R_5$ are hydrogen, and $R_1$ and $R_2$ independently represent hydroxy or methoxy.

32. A process according to claim 23, wherein, in the compound of formula (I), $R_3$ is hydrogen.

33. A process according to claim 23, wherein, in the compound of formula (I), $R_3$ is ethylidene.

34. A process according to claim 23, wherein, in the compound of formula (I), $R_3$ is R form or S form of hydroxyl or alkoxy.

35. A process according to claim 23, wherein the optional step is carried out in the presence of 1,4-cyclohexadiene.

* * * * *